United States Patent
Liang

(10) Patent No.: US 9,242,958 B2
(45) Date of Patent: Jan. 26, 2016

(54) SUBSTITUTED PYRIDAZINE CARBOXAMIDE COMPOUNDS AS KINASE INHIBITOR COMPOUNDS

(75) Inventor: Congxin Liang, Palm Beach Gardens, FL (US)

(73) Assignee: Xcovery Holding Company LLC, Palm Beach Gardens, FL (US)

(*) Notice: Subject to any disclaimer, the term of this patent is extended or adjusted under 35 U.S.C. 154(b) by 68 days.

(21) Appl. No.: 13/877,812

(22) PCT Filed: Oct. 7, 2011

(86) PCT No.: PCT/US2011/055427
§ 371 (c)(1),
(2), (4) Date: Apr. 4, 2013

(87) PCT Pub. No.: WO2012/048258
PCT Pub. Date: Apr. 12, 2012

(65) Prior Publication Data
US 2013/0203763 A1    Aug. 8, 2013

Related U.S. Application Data

(60) Provisional application No. 61/391,464, filed on Oct. 8, 2010.

(51) Int. Cl.
*C07D 401/12* (2006.01)
*C07D 237/24* (2006.01)

(52) U.S. Cl.
CPC .......... *C07D 401/12* (2013.01); *C07D 237/24* (2013.01)

(58) Field of Classification Search
CPC .......................... C07D 401/12; C07D 237/24
See application file for complete search history.

(56) References Cited

U.S. PATENT DOCUMENTS

2010/0063031 A1    3/2010  Liang

FOREIGN PATENT DOCUMENTS

| JP | 2010516680 A | 5/2010 |
|---|---|---|
| WO | WO-2006021886 A1 | 3/2006 |
| WO | WO-2008/088881 A1 | 7/2008 |
| WO | WO-2009154769 A1 | 12/2009 |

OTHER PUBLICATIONS

International Search Report of PCT/US2011/055427.
Japanese Office Action for Japanese Application No. 2013-532984 dated Jun. 30, 2015.

*Primary Examiner* — Savitha Rao
*Assistant Examiner* — Angela Brown-Pettigrew
(74) *Attorney, Agent, or Firm* — Wolf, Greenfield & Sacks, P.C.

(57) ABSTRACT

The new pyridazine derivatives have unexpected drug properties as inhibitors of protein kinases especially against c-Met and are useful in treating disorders related to abnormal protein kinase activities such as cancer.

7 Claims, 2 Drawing Sheets

Expression of phospho-c-Met and c-Met in tumor cell lines

Figure 1. Expression of phospho-c-Met and c-Met in tumor cell lines
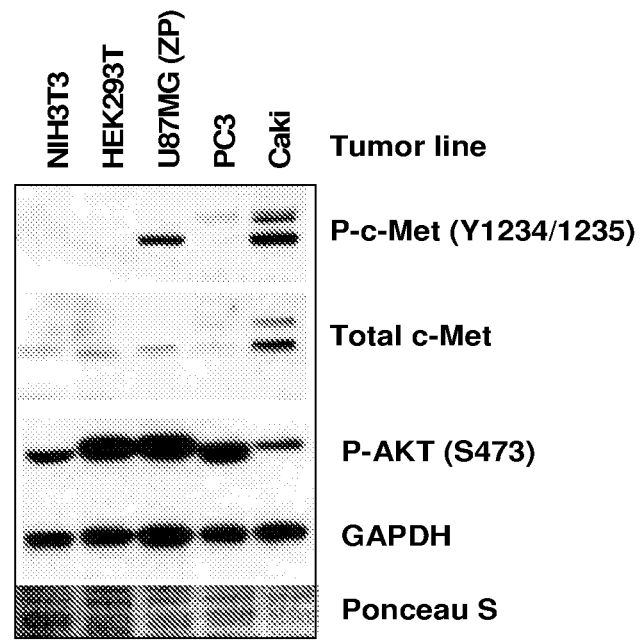

Figure 2. Growth inhibition of EXAMPLE 1 on U-87 MG xenograft tumor model. The data graph shows the tumor volume of U-87 MG in Balb/c nude mice. Lines, mean tumor volume for each group, bars, ±S.E.
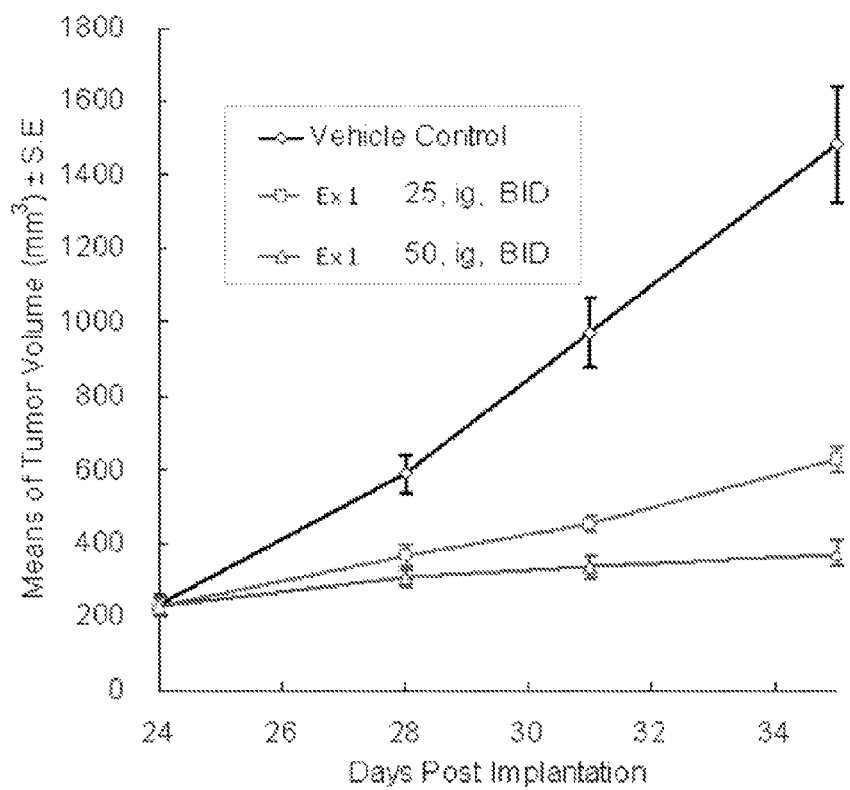

SUBSTITUTED PYRIDAZINE CARBOXAMIDE COMPOUNDS AS KINASE INHIBITOR COMPOUNDS

RELATED APPLICATIONS

This application claims the benefit of U.S. Provisional application 61/391,464, filed on Oct. 8, 2010, the contents of which are incorporated in its entirety.

TECHNICAL FIELD OF THE INVENTION

This invention relates to novel pyridazine derivatives, their salts, solvates, hydrates and polymorphs thereof. The invention also provides compositions comprising a compound of this invention and the use of such compositions in methods of treating diseases and conditions associated with protein kinase modulation.

BACKGROUND OF THE INVENTION

Protein kinases are enzymes that catalyze the phosphorylation of hydroxyl groups of tyrosine, serine, and threonine residues of proteins. Many aspects of cell life (for example, cell growth, differentiation, proliferation, cell cycle and survival) depend on protein kinase activities. Furthermore, abnormal protein kinase activity has been related to a host of disorders such as cancer and inflammation. Therefore, considerable effort has been directed to identifying ways to modulate protein kinase activities. In particular, many attempts have been made to identify small molecules that act as protein kinase inhibitors.

The c-Met proto-oncogene encodes the Met receptor tyrosine kinase. The Met receptor is a 190 kDa glycosylated dimeric complex composed of a 50 kDa alpha chain disulfide-linked to a 145 kDa beta chain. The alpha chain is found extracellularly while the beta chain contains transmembrane and cytosolic domains. Met is synthesized as a precursor and is proteolytically cleaved to yield mature alpha and beta subunits. It displays structural similarities to semaphorins and plexins, a ligand-receptor family that is involved in cell-cell interaction. The ligand for Met is hepatocyte growth factor (HGF), a member of the scatter factor family and has some homology to plasminogen (Longati, P. et al., Curr. Drug Targets 2001, 2, 41-55); Trusolino, L. and Comoglio, P. Nature Rev. Cancer 2002, 2, 289-300].

Met functions in tumorigenesis and tumor metastasis. Expression of Met along with its ligand HGF is transforming, tumorigenic, and metastatic (Jeffers, M. et al., Oncogene 1996, 13, 853-856; Michieli, P. et al., Oncogene 1999, 18, 5221-5231). MET is overexpressed in a significant percentage of human cancers and is amplified during the transition between primary tumors and metastasis. Numerous studies have correlated the expression of c-MET and/or HGF/SF with the state of disease progression of different types of cancer (including lung, colon, breast, prostate, liver, pancreas, brain, kidney, ovaries, stomach, skin, and bone cancers). Furthermore, the overexpression of c-MET or HGF have been shown to correlate with poor prognosis and disease outcome in a number of major human cancers including lung, liver, gastric, and breast. c-MET has also been directly implicated in cancers without a successful treatment regimen such as pancreatic cancer, glioma, and hepatocellular carcinoma.

Met mutants exhibiting enhanced kinase activity have been identified in both hereditary and sporadic forms of papillary renal carcinoma (Schmidt, L. et al., Nat. Genet. 1997, 16, 68-73; Jeffers, M. et al., Proc. Nat. Acad. Sci. 1997, 94, 11445-11500). HGF/Met has been shown to inhibit anoikis, suspension-induced programmed cell death (apoptosis), in head and neck squamous cell carcinoma cells. Anoikis resistance or anchorage-independent survival is a hallmark of oncogenic transformation of epithelial cells (Zeng, Q. et al., J. Biol. Chem. 2002, 277, 25203-25208).

Increased expression of Met/HGF is seen in many metastatic tumors including colon (Fazekas, K. et al., Clin. Exp. Metastasis 2000, 18, 639-649), breast (Elliott, B. E. et al., 2002, Can. J. Physiol. Pharmacol. 80, 91-102), prostate (Knudsen, B. S. et al., Urology 2002, 60, 1113-1117), lung (Siegfried, J. M. et al., Ann. Thorac. Surg. 1998, 66, 1915-1918), and gastric (Amemiya, H. et al., Oncology 2002, 63, 286-296). HGF-Met signaling has also been associated with increased risk of atherosclerosis (Yamamoto, Y. et al., J. Hypertens. 2001, 19, 1975-1979; Morishita, R. et al., Endocr. J. 2002, 49, 273-284) and increased fibrosis of the lung (Crestani, B. et al., Lab. Invest. 2002, 82, 1015-1022).

2-amino-pyridines, such as PF-2341066, have been reported as potent inhibitors of the HGF receptor tyrosine kinase (c-Met) and ALK (J. G. Christensen, et al. Abstract LB-271, AACR 2006 meeting; H. Y. Zou et al. Cancer Res 2007; 67: 4408; patent disclosures: WO 2004076412, WO 2006021881, WO 2006021886).

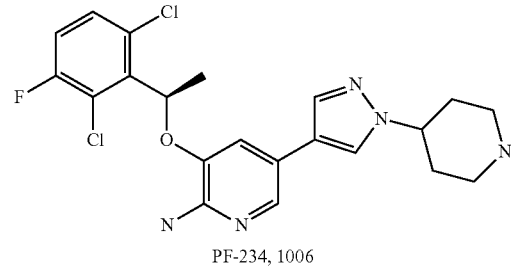 [SMILES: C[C@@H](Oc1cc(-c2cnn(C3CCNCC3)c2)cnc1N)c1c(Cl)ccc(F)c1Cl]

PF-234,1006

Previously, we described the substituted pyridazine carboxamide compounds as protein kinase inhibitors (WO 2009/154769). Most of these compounds potently inhibit c-Met and ALK with IC50 of <100 nM. This invention discloses the unsaturated heterocycle substituted pyridazine carboxamide as more selective c-Met inhibitors.

SUMMARY OF THE INVENTION

The invention relates to pyridazine derivative compounds (e.g., any of the formulae herein), compositions comprising the compounds, and methods of using the compounds and compound compositions. The compounds and compositions comprising them are useful for treating or preventing disease or disease symptoms, including those mediated by or associated with protein kinase modulation activity.

The present invention solves the problems set forth above by providing an isolated compound of Formula I

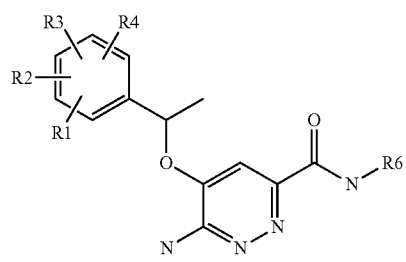

or a salt thereof; or a prodrug, or a salt of a prodrug thereof; or a hydrate, solvate, or polymorph thereof; wherein:

$R_1$, $R_2$, $R_3$, and $R_4$ each are independently H, alkyl, or $Z^1$;

$R_6$ is an unsaturated heterocyclyl, wherein $R_6$ is optionally substituted by 1-3 groups independently selected from alkyl, cycloalkyl, heterocyclyl, alkoxy, hydroxyalkyl, and $Z^1$;

Each $Z^1$ is halogen, CN, $NO_2$, $OR^{15}$, $SR^{15}$, $S(O)_2OR^1$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where each n is independently 0-6;

Each $R^{15}$ is independently hydrogen, $C_1$-$C_4$ alkyl or $C_3$-$C_6$ cycloalkyl;

Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl; and Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl.

The compounds of this invention, and compositions comprising them, are useful for treating or lessening the severity of protein kinase modulated diseases, disorders, or symptoms thereof, i.e., disorders effectively treated by inhibitors of protein kinases, especially c-met.

In another aspect, the invention relates to a method of treating a disease or disease symptom in a subject in need thereof including administering to the subject an effective amount of a compound of any formulae herein, or pharmaceutical salt, solvate or hydrate thereof (or composition thereof). The disease or disease symptom can be any of those modulated by a protein kinase (e.g. c-met). The disease or disease symptom can be, for example, cancer or proliferation disease or disorder (e.g., including those delineated herein).

DETAILED DESCRIPTION OF THE INVENTION

Description of the Drawings

FIG. 1 showed c-Met expression in all these cell lines. U87MG, PC3 and Caki cells expressed phosphorylated high level of c-Met. Compared to total c-Met expression level, U87-MG showed the most elevated phospho-c-Met level and thus it was selected for in vivo studies.

FIG. 2. Growth inhibition of EXAMPLE 1 on U-87 MG xenograft tumor model. The data graph shows the tumor volume of U-87 MG in Balb/c nude mice. Lines, mean tumor volume for each group, bars, ±S.E.

DEFINITIONS

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

By "marker" is meant any alteration that is associated with a disease or disorder.

For example, any protein or polynucleotide having an alteration in expression level or activity that is associated with a disease or disorder.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The term "compound" as used herein, is also intended to include salts, prodrugs, and prodrug salts of a compound of formulae herein. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as amides, esters, carbamates, carbonates, and phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the term "biohydrolyzable moiety" means a functional group (e.g., amide, ester, carbamate, carbonate, or phosphate analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A prodrug salt is a compound formed between an acid and a basic group of the prodrug, such as an amino functional group, or a base and an acidic group of the prodrug, such as a carboxyl functional group. In a one embodiment, the prodrug salt is a pharmaceutically acceptable salt.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X" % of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers.

As used herein, the term "halo" or "halogen" refers to any radical of fluorine, chlorine, bromine or iodine.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms (inclusive).

The term "arylalkyl" refers to a moiety in which an alkyl hydrogen atom is replaced by an aryl group.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkoxy" refers to an —O-alkyl radical. The term "alkylenedioxo" refers to a divalent species of the structure —O—R—O—, in which R represents an alkylene.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a divalent straight chain bridge of 1 to 5 carbon atoms connected by single bonds (e.g., —$(CH_2)_x$—, wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —$C(CH_3)_2$CH=CH— and —CH($C_2H_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH($CH_3$)C≡C— and —C≡C—CH($C_2H_5$)$CH_2$—.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbon.

The terms "Ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples, without limitation, of heteroaryl groups are pyrrole, furan, thiophene, imidazole, oxazole, thiazole, pyrazole, pyridine, pyrimidine, quinoline, quinazoline, isoquinoline, purine and carbazole.

The terms "heterocycle", "heterocyclic" or "heterocyclo" refer to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

The term "heterocyclyl" refers to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclyl group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclyl group may be attached at any heteroatom or carbon atom of the ring or ring system.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. Suitable substituents include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where n is independently 0-6 inclusive. Each $R^{15}$ is independently hydrogen, $C_1$-$C_4$ alkyl or $C_3$-$C_6$ cycloalkyl. Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^5$, $R^{16}$ and $R^{17}$ can optionally be substituted with halogen, CN, $C_1$-$C_4$ alkyl, OH, $C_1$-$C_4$ alkoxy, $NH_2$, $C_1$-$C_4$ alkylamino, $C_1$-$C_4$ dialkylamino, $C_1$-$C_2$ perfluoroalkyl, $C_1$-$C_2$ perfluoroalkoxy, or 1,2-methylenedioxy.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

Compounds of the Invention

In one aspect, the present invention provides a compound of Formula I:

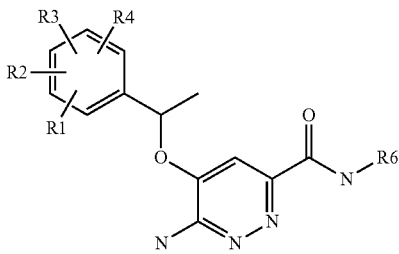

or a salt thereof; or a prodrug, or a salt of a prodrug thereof; or a hydrate, solvate, or polymorph thereof; wherein:

$R_1$, $R_2$, $R_3$, and $R_4$ each are independently H, alkyl, or $Z^1$;

$R_6$ is an unsaturated heterocyclyl, wherein $R_6$ is optionally substituted by 1-3 groups, independently selected from alkyl, cycloalkyl, heterocyclyl, alkoxy, hydroxyalkyl, and $Z^1$;

Each $Z^1$ is halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where each n is independently 0-6;

Each $R^{15}$ is independently hydrogen, $C_1$-$C_4$ alkyl or $C_3$-$C_6$ cycloalkyl;

Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl; and Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl.

In one embodiment, the invention provides for a compound of formula II:

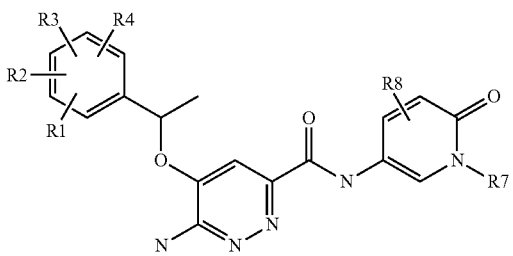

or a salt thereof; or a prodrug, or a salt of a prodrug thereof; or a hydrate, solvate, or polymorph thereof; wherein $R_1$, $R_2$, $R_3$, $R_4$, $R_7$ and $R_8$ each are independently H, alkyl or $Z^1$;

Each $Z^1$ is halogen, CN, $NO_2$, $OR^{15}$, $SR^{15}$, $S(O)_2OR^5$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where each n is independently 0-6;

Each $R^{15}$ is independently hydrogen, $C_1$-$C_4$ alkyl or $C_3$-$C_6$ cycloalkyl;

Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl; and Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl.

In another embodiment, the invention provides for a compound of formula III:

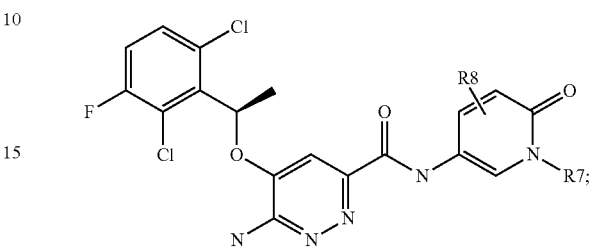

or a salt thereof; or a prodrug, or a salt of a prodrug thereof; or a hydrate, solvate, or polymorph thereof; wherein $R_7$ and $R_8$ each are independently H, alkyl or $Z^1$;

Each $Z^1$ is halogen, CN, $NO_2$, $OR^{15}$, $SR^{15}$, $S(O)_2OR^5$, $NR^{15}R^{16}$, $C_1$-$C_2$ perfluoroalkyl, $C_1$-$C_2$ perfluoroalkoxy, 1,2-methylenedioxy, $C(O)OR^5$, $C(O)NR^{15}R^{16}$ $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where each n is independently 0-6;

Each $R^{15}$ is independently hydrogen, $C_1$-$C_4$ alkyl or $C_3$-$C_6$ cycloalkyl;

Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl; and Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl.

Representative compounds of the invention are depicted in Table 1. In these examples the stereochemistry at the chiral carbon atoms is independently either RS, R, or S, unless specified. The structures depicted herein, including the Table 1 structures, may contain certain —NH—, —NH$_2$ (amino) and —OH (hydroxyl) groups where the corresponding hydrogen atom(s) do not explicitly appear; however they are to be read as —NH—, —NH$_2$ or —OH as the case may be. In certain structures, a stick bond is drawn and is meant to depict a methyl group.

TABLE 1

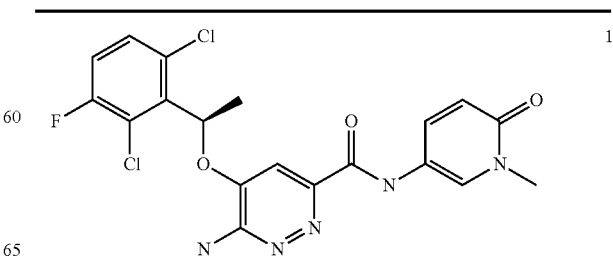

TABLE 1-continued

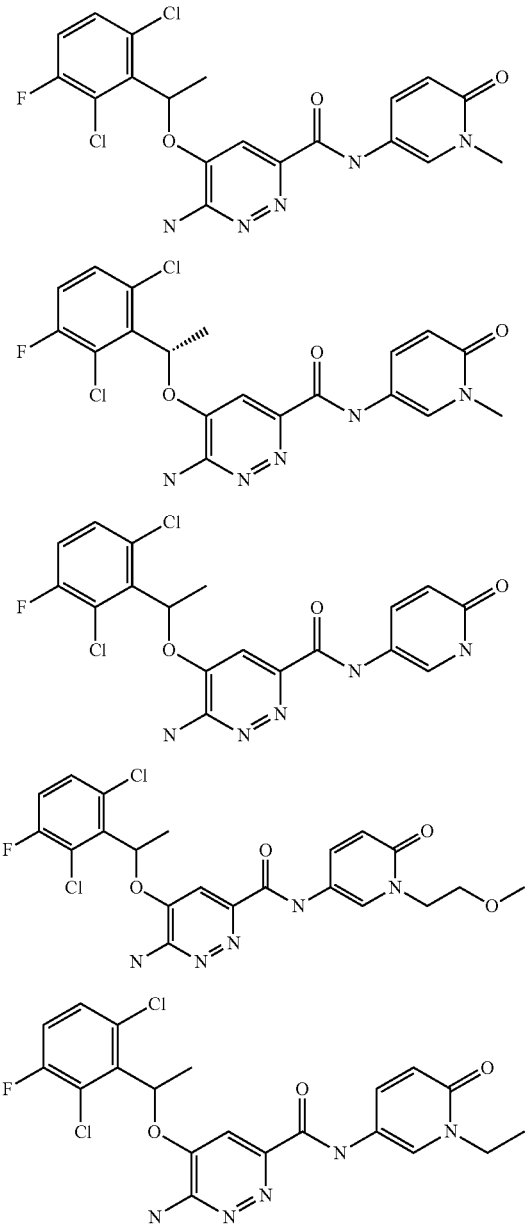

Representative compounds of the invention are listed below:
{5-[(1R)-1-(2,6-dichloro-3-fluorophenyl)ethoxy]-6-aminopyridazin-3-yl}-N-(1-methyl-6-oxo-1,6-dihydro-pyridin-3-yl)carboxamide;
{6-amino-5-[(2,6-dichloro-3-fluorophenyl)ethoxy]pyridazin-3-yl}-N-(1-methyl-6-oxo-1,6-dihydro-pyridin-3-yl)carboxamide;
{5-[(1S)-1-(2,6-dichloro-3-fluorophenyl)ethoxy]-6-aminopyridazin-3-yl}-N-(1-methyl-6-oxo-1,6-dihydro-pyridin-3-yl)carboxamide;
{6-amino-5-[(2,6-dichloro-3-fluorophenyl)ethoxy]pyridazin-3-yl}-N-(6-oxo-1,6-dihydro-pyridin-3-yl)carboxamide;
{6-amino-5-[(2,6-dichloro-3-fluorophenyl)ethoxy]pyridazin-3-yl}-N-[1-(2-methoxyethyl)-6-oxo-1,6-dihydro-pyridin-3-yl]carboxamide;
{6-amino-5-[(2,6-dichloro-3-fluorophenyl)ethoxy]pyridazin-3-yl}-N-(1-ethyl-6-oxo-1,6-dihydro-pyridin-3-yl)carboxamide.

The synthesis of compounds of the formulae herein can be readily effected by synthetic chemists of ordinary skill. Relevant procedures and intermediates are disclosed, for instance, herein. Each of the patents, patent applications, and publications, whether in traditional journals or available only through the internet, referred to herein, is incorporated in its entirety by reference.

Other approaches to synthesizing compounds of the formulae herein can readily be adapted from references cited herein. Variations of these procedures and their optimization are within the skill of the ordinary practitioner.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $R^1$, $R^2$, R, R', X, etc.) or not. The suitability of a chemical group in a compound structure for use in synthesis of another compound structure is within the knowledge of one of ordinary skill in the art. Additional methods of synthesizing compounds of the formulae herein and their synthetic precursors, including those within routes not explicitly shown in schemes herein, are within the means of chemists of ordinary skill in the art. Methods for optimizing reaction conditions, if necessary minimizing competing by-products, are known in the art. The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Combinations of substituents and variables envisioned by this invention are only those that result in the formation of stable compounds.

The invention also provides compositions comprising an effective amount of a compound of any of the formulae herein, or a pharmaceutically acceptable salt, solvate, hydrate, polymorph or prodrug, if applicable, of said compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528,080, 6,800,663, and references cited therein). A useful formulation for the compounds of this invention is the form of enteric pellets of which the enteric layer comprises hydroxypropylmethylcellulose acetate succinate.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. A *Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

In another embodiment, a composition of the present invention further comprises a second therapeutic agent. The second therapeutic agent includes any compound or therapeutic agent known to have or that demonstrates advantageous properties when administered alone or with a compound of any of the formulae herein. Drugs that could be usefully combined with these compounds include other kinase inhibitors and/or other chemotherapeutic agents for the treatment of the diseases and disorders discussed above.

Such agents are described in detail in the art. Preferably, the second therapeutic agent is an agent useful in the treatment or prevention of a disease or condition selected from cancer.

Even more preferably the second therapeutic agent co-formulated with a compound of this invention is an agent useful in the treatment of c-met, ron, or ALK and its fusion proteins such as EML4-ALK and NPM-ALK mediated disease/disorders. Even more preferably the second therapeutic agent co-formulated with a compound of this invention is an agent useful in the treatment of c-met mediated disorder.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, more preferably 0.1 mg/kg to about 2.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease or disorder or symptom thereof (e.g., those delineated herein) comprising the step of administering to said subject an effective amount of a compound or a composition of this invention. Such diseases are well known in the art and are also disclosed herein.

In one aspect, the method of treating involves treatment of a disorder that is mediated by the protein kinase, e.g. c-met, ron.

In another aspect, the invention provides a method of treating a disease in a subject comprising administering to the subject a compound of any of the formulae herein.

In another aspect, invention provides a method of treating a disease in a subject comprising administering to the subject a composition comprising a compound of any of the formulae herein.

In certain embodiments, the disease is mediated by the c-met or ron kinases.

In another embodiment, the disease is cancer or a proliferation disease.

In yet another embodiment, the disease is cancer of the lung, colon, breast, prostate, liver, pancreas, brain, kidney, ovaries, stomach, or skin, or bone cancers, gastric cancer, breast cancer, pancreatic cancer, glioma, and hepatocellular carcinoma, papillary renal carcinoma, or head and neck squamous cell carcinoma.

In a one embodiment, the method of this invention is used to treat a subject suffering from or susceptible to a disease or condition. Such diseases, disorders or symptoms thereof include, for example, those modulated by a protein kinase (e.g., c-met, ron). The disease or disease symptom can be, for example, cancer or proliferation disease or disorder. The disease or disease symptom can be lung, colon, breast, prostate, liver, pancreas, brain, kidney, ovaries, stomach, skin, and bone cancers, gastric cancer, breast cancer, pancreatic cancer, glioma, and hepatocellular carcinoma, papillary renal carcinoma, or head and neck squamous cell carcinoma. Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, the invention provides a method of modulating the activity of a protein kinase (e.g. protein tyrosine kinase, kinases listed herein) in a cell comprising contacting a cell with one or more compounds of any of the formulae herein.

In another embodiment, the above method of treatment comprises the further step of co-administering to said patient one or more second therapeutic agents. The choice of second therapeutic agent may be made from any second therapeutic agent known to be useful for indications herein. Additional therapeutic agents include but are not limited to agents for treatment of diseases, disorders or symptoms thereof including for example, anticancer agents, antiproliferative agents, antineoplastic agents, antitumor agents, antimetabolite-type/thymidilate synthase inhibitor antineoplastic agents, alkylating-type antineoplastic agents, antibiotic-type antineoplastic agents, or, any other agent typically administered as a primary or adjuvant agent in cancer treatment protocols (e.g., antinausea, antianemia, etc.), including for example, vinblastine sulfate, vincristine, vindesine, vinestramide, vinorelbine, vintriptol, vinzolidine, tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone, Iressa, Avastin, OSI-774, angiogenesis inhibitors, EGFR inhibitors, MEK inhibitors, VEGFR inhibitors, CDK inhibitors, Her1 and Her2 inhibitors and monoclonal antibodies.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of any of the formulae herein alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

The present invention also provides kits for use to treat diseases, disorders, or symptoms thereof, including those delineated herein. These kits comprise: a) a pharmaceutical composition comprising a compound of any of the formula herein or a salt thereof; or a prodrug, or a salt of a prodrug thereof; or a hydrate, solvate, or polymorph thereof, wherein said pharmaceutical composition is in a container; and b) instructions describing a method of using the pharmaceutical composition to treat the disease, disorder, or symptoms thereof, including those delineated herein.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kit may additionally comprising information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information.

The compounds delineated herein can be assessed for their biological activity using protocols known in the art, including for example, those delineated herein. Certain of the compounds herein demonstrate unexpectedly superior attributes (e.g., inhibition of P450, Met, Ron, etc.; pharmacokinetic properties, etc.) making them superior candidates as potential therapeutic agents.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EXAMPLES

Synthesis of 5-[(2,6-dichloro-3-fluorophenyl)ethoxy]-6-{(tert-butoxy)-N-[(tert-butyl)oxycarbonyl]carbonylamino}pyridazine-3-carboxylic acid (A)

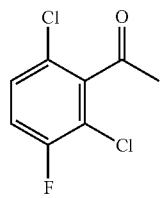

A4

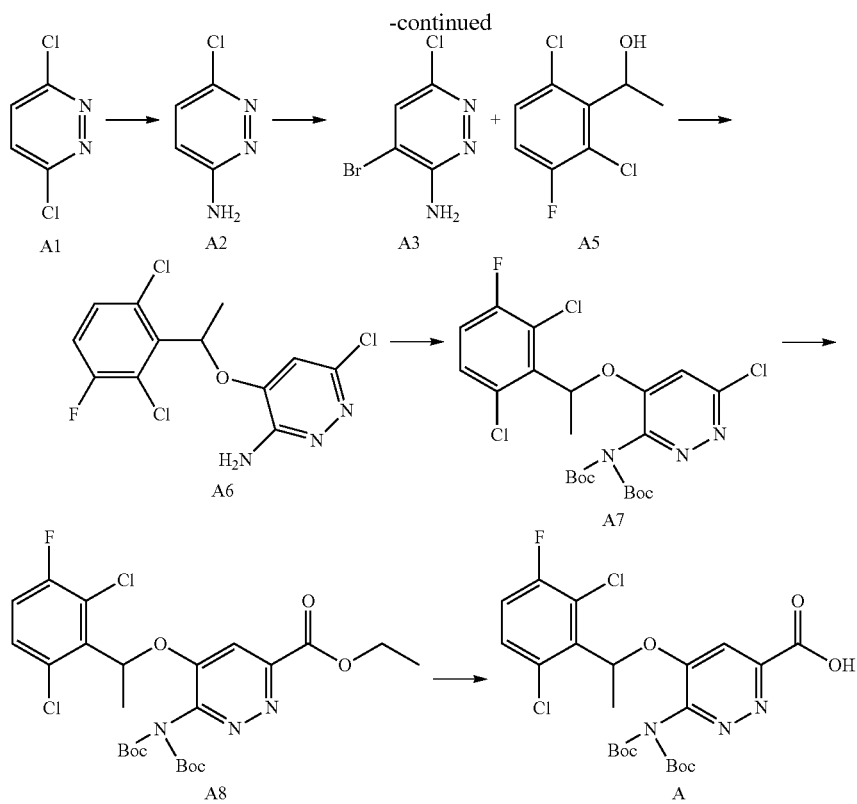

Step 1: A suspension of A1 (400 g, 2.68 mol) in 25% ammonium hydroxide (3 L) was heated at 130° C. for 12 h in a sealed stainless autoclave. After the tube was cooled to 0° C., the mixture was filtered. The resulting solid was washed with water for several times and dried under vacuo to provide A2 (284 g, 82%).

Step 2: To a solution of A2 (284 g, 2.19 mol) in methanol (3.5 L) was added NaHCO$_3$ (368.4 g, 4.38 mol) at room temperature, followed by bromine (350 g, 2.19 mol) dropwise. After the addition was complete, the mixture was stirred for 20 h, then filtered and washed by methanol for several times. The filtrate was concentrated and the residue was dissolved in water (2 L) and extracted with ethyl acetate (2 L×3). The combined organic phase was washed with 10% sodium thiosulfate aq. (2 L), sat. sodium bicarbonate aq. (2 L) and brine (2 L), dried over anhydrous magnesium sulfate and evaporated. The residue was purified by column chromatography (EA:PE=2:1) to provide A3 (159.8 g, 35%).

Step 3: To a solution of A4 (150 g, 0.72 mol) in methanol (800 mL) cooled to 0° C., was added NaBH$_4$ (66 g, 1.74 mol) in portions. The resulting mixture was stirred at r.t. for about 1 h and evaporated. Water (1 L) was added to the residue at 0° C., followed by 3N HCl until pH=6. The resulting mixture was extracted with ethyl acetate (400 mL×4). The combined organic phase was dried over anhydrous sodium sulfate, filtered and concentrated to give A5 (148.6 g, 98%).

Step 4: To a solution of A5 (147.6 g, 0.71 mol) in THF (3 L) was added 60% NaH (28.4 g, 0.71 mol) at 0° C., the resulting mixture was stirred at that temperature for 30 min, was then added A3 (147 g, 0.71 mmol) quickly. The resulting mixture was heated under reflux overnight and evaporated. The residue was purified by column chromatography (PE:EA=4:1) to provide the advanced intermediate A6 (89.3 g, 37.6%).

Step 5: To a solution of A6 (97 g, 0.288 mol) in DMF (1 L) was added Boc$_2$O (113 g, 0.519 mol) and DMAP (7 g, 58 mmol). The mixture was stirred at r.t. overnight and evaporated. The residue was purified by column chromatography (PE:EA=10:1) to afford A7 (136 g, 88%).

Step 6: Sodium acetate (41 g, 0.50 mol) was added to a solution of A7 (136 g, 0.25 mol) in ethanol/DMF [(5:1) (1200 mL)]. The mixture was degassed, then added Pd(dppf)Cl$_2$.CH$_2$Cl$_2$ (18.63 g, 22.5 mmol). The resulting mixture was heated at CO atmosphere at 90° C. for 1.5 h, then evaporated. The residue was purified by column chromatography (PE:EA=1:4) to afford A8 (141 g, 97%).

Step 7: To the solution of A8 (141 g, 0.246 mol) in THF (650 mL) was added 1N LiOH aq. (390 mL). The resulting mixture was stirred at r.t. over weekend, then acidified by 2N HCl to pH=5, extracted with ethyl acetate (300 mL×5). The combined organic phase was dried over Na$_2$SO$_4$, filtered and concentrated to give A (134 g, 99%).

Synthesis of 6-[bis(tert-butoxycarbonyl)amino]-5-[(1R)-1-(2,6-dichloro-3-fluoro-phenyl)ethoxy]pyridazine-3-carboxylic acid (B)

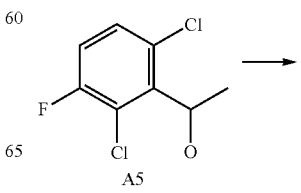

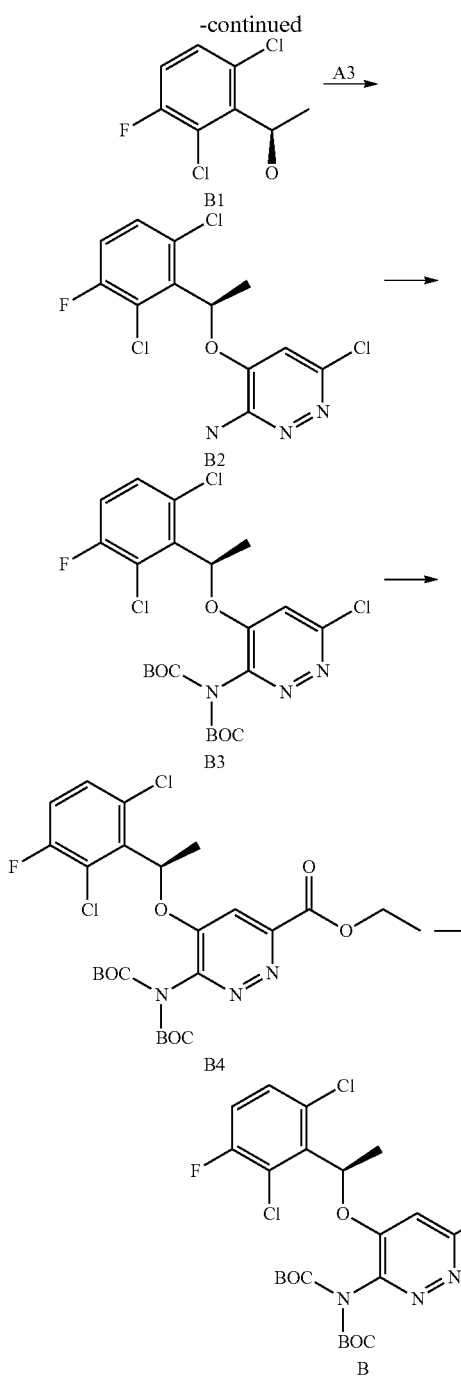

raphy (PE:EA=4:1) to provide the advanced intermediate B2 (33.95 g, 37.7%). 1H-NMR (300 MHz, CDCl₃): δ=1.87 (d, 3H), 5.08 (s, 2H), 6.03-6.09 (m, 1H), 6.42 (s, 1H), 7.14 (t, 1H), 7.35 (dd, 1H). LC-MS [M+H]⁺: 336.0.

Step 3: To a solution of B2 (33.95 g, 101 mmol) in DMF (400 mL) was added BOC₂O (39.59 g, 182 mmol) and DMAP (2.46 g, 20.2 mmol). The mixture was stirred at r.t. overnight and evaporated. The residue was purified by column chromatography (PE:EA=10:1) and the residue was treated with PE:EA=10:1 to afford B3 (46.9 g, 86.7%).

Step 4: Sodium acetate (14.34 g, 175 mmol) was added to a solution of B3 (46.9 g, 87.4 mmol) in ethanol/DMF [(5:1) (480 mL)]. The mixture was degassed, then added Pd(dppf) Cl₂.CH₂Cl₂ (7.14 g, 8.74 mmol). The resulting mixture was heated at CO atmosphere at 90° C. overnight, then evaporated. The residue was purified by column chromatography (PE:EA=4:1) to afford B4 (47.1 g, 94.0%). 1H-NMR (300 MHz, CDCl₃): δ=1.38 (s, 18H), 1.46 (t, 3H), 1.88 (d, 3H), 4.45-4.53 (m, 2H), 6.18 (q, 1H), 7.13 (t, 1H), 7.34 (dd, 1H), 7.57 (s, 1H). LC-MS [M+H]⁺: 574.0.

Step 5: To the solution of B4 (47.1 g, 82.1 mmol) in THF (400 mL) was added 1N LiOH aq. (98.5 mL). The resulting mixture was stirred at r.t. over weekend, then acidified by 2N HCl to pH=5, extracted with ethyl acetate (400 mL×3). The combined organic phase was dried over Na₂SO₄, filtrated and concentrated to give B (45.94 g, ~100%).

Synthesis of 6-[bis(tert-butoxycarbonyl)amino]-5-[(1S)-1-(2,6-dichloro-3-fluoro-phenyl)ethoxy]pyridazine-3-carboxylic acid (C)

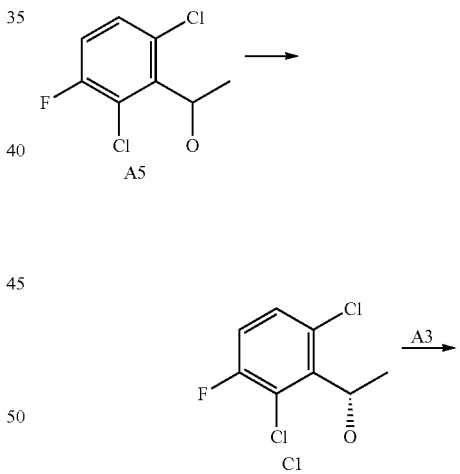

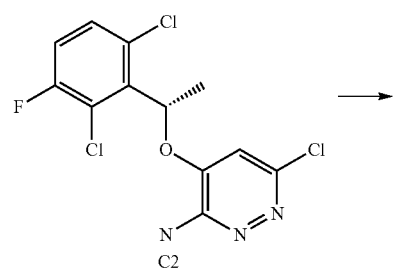

Step 1: To a solution of A5 (219 g, 1.05 mol) in 1,2-dichloroethane (3500 mL) was added Boc-D-Pro (141 g, 0.65 mol) followed by EDCI (163 g, 0.85 mol) and DMAP (21.57 g, 0.18 mol) at 0° C. The resulting mixture was stirred at r.t. overnight and then water (3500 mL) was added and separated, the water phase was extracted with DCM (1500 mL×3), dried over MgSO₄, concentrated and purified by column chromatography to (PE:EA=30:1) to give B1 (55.96 g, yield: 51.1%)

Step 2: To a solution of B1 (59.96 g, 268 mmol) in THF (1200 mL) was added 60% NaH (10.71 g, 268 mmol) at 0° C., the resulting mixture was stirred at that temperature for 30 min, was then added A3 (55.82 g, 268 mmol) quickly. The resulting mixture was heated under reflux overnight and evaporated. The residue was purified by column chromatog-

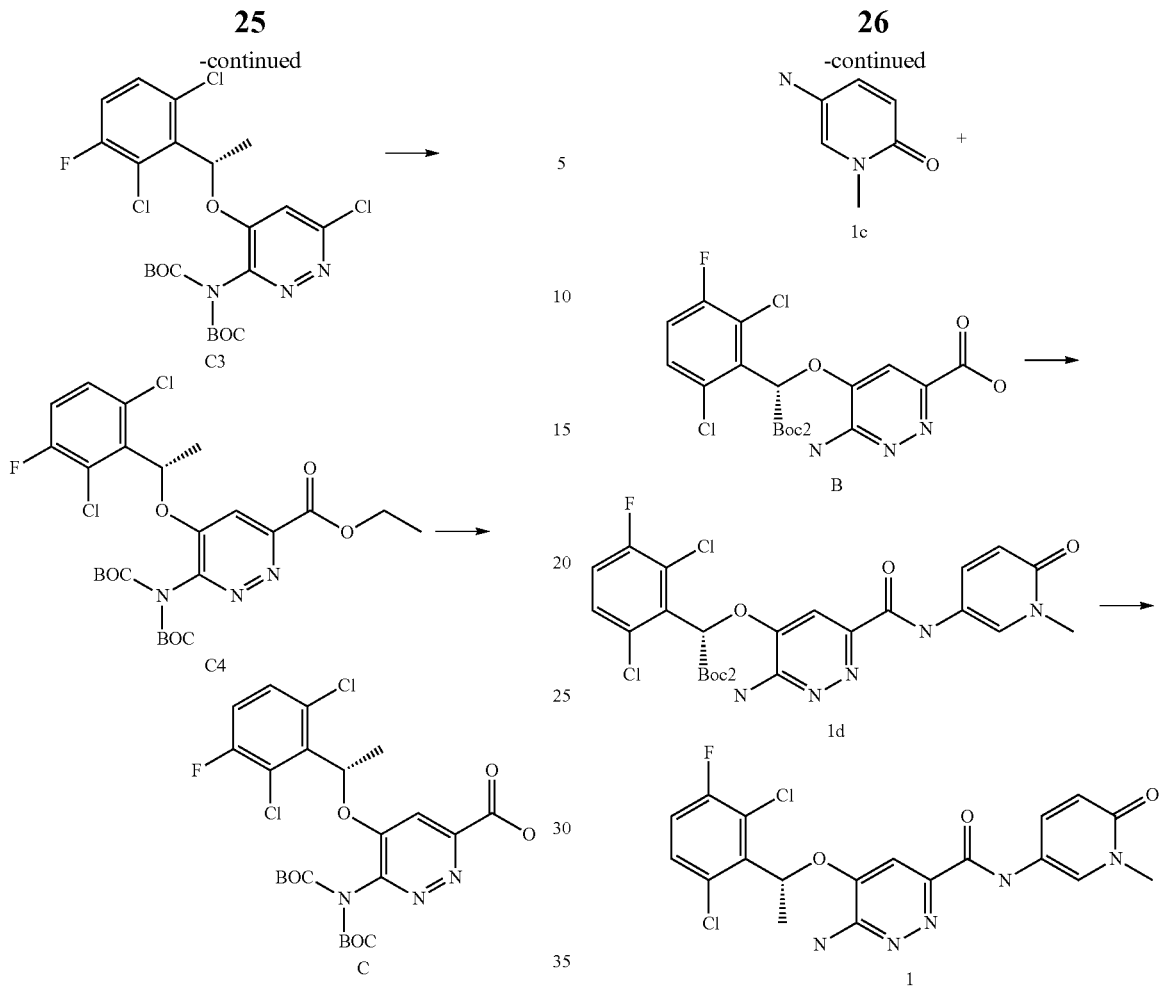

Step 1: To a solution of A5 (41.8 g, 200 mmol) in 1,2-dichloroethane (800 mL) was added Boc-L-Pro (26.9 g, 125 mmol) followed by EDCI (31.1 g, 163 mmol) and DMAP (4.12 g, 33.8 mmol) at 0° C. The resulting mixture was stirred at r.t. overnight and then water (350 mL) was added and separated, the water phase was extracted with DCM (150 mL×3), dried over MgSO$_4$, concentrated and purified by column chromatography to (PE:EA=30:1) to give C1 (13.72 g, yield: 65.6%).

Step 2: The procedure from C1 to C was similar to that of B1 to B (9.46 g, yield: 26.4% from C1).

Example 1

Synthesis of {5-[(1R)-1-(2,6-dichloro-3-fluorophenyl)ethoxy]-6-aminopyridazin-3-yl}-N-(1-methyl-6-oxo-1,6-dihydro-pyridin-3-yl)carboxamide

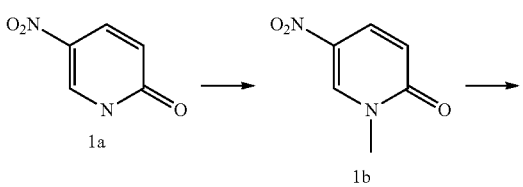

Step 1: To a solution of 1a (16.0 g, 114 mmol) in DMF (500 mL) was added NaH (5.5 g, 137 mmol). The suspension was stirred at 0° C. for 0.5 h and added CH$_3$I (17.8 g, 126 mmol) dropwise at 0° C. The resulting mixture was allowed to warm to r.t. for 1 h and evaporated. The residue was added sat. NaHCO$_3$ (50 mL) and water (50 mL). The suspension was extracted with DCM (300 mL) twice. The combined extract was washed water, dried over MgSO$_4$ and concentrated. The residue was retreated with PE:EA=10:1 to provide 1b (11.05 g, 63.0%).

Step 2: Reductive iron powder (39.0 g, 69.6 mmol) and 2N HCl (20 mL) were added to a stirred solution of 1b (15.4 g, 100 mmol) in ethanol (300 mL) at 0° C. The resulting mixture was heated under reflux for 2 h and filtrated. The brown solid was washed with ethanol for several times. The combined ethanol phase was evaporated and the residue was dissolved in ethyl acetate (400 mL) and washed with 1.5N Na$_2$CO$_3$ aq. (400 mL). The bi-phase mixture was separated and the water phase was re-extracted with ethyl acetate (250 mL×3). The combined organic phase was dried over MgSO$_4$, filtered and evaporated to give 1c (10.0 g, 80.6%).

Step 11: The mixture of B (20.00 g, 36.6 mmol), HATU (28.00 g, 73.7 mmol) and DIEA (14 g, 108.5 mmol) in DMF (200 mL) was stirred at room temperature for 0.5 h, then was added 1c (10 g, 81.9 mmol). The resulting mixture was stirred at room temperature for 0.5 h and evaporated. The residue was purified by column chromatography (EA:MeOH=5:1) to provide 1d (18.0 g, 75.4%).

Step 12: 1d (18.0 g, 27.6 mmol) was dissolved in a mixture of DCM (150 mL) and TFA (50 mL), stirred at r.t. for 2 hours and evaporated. The residue was adjusted by sat. Na$_2$CO$_3$ to pH=8 and extracted with DCM (200 mL×5). The combined organic phase was dried over MgSO$_4$ and concentrated. The residue was triturated with methanol and filtered, then the solid was dissolved in DCM and a solution of HCl in Et$_2$O was added, the mixture was stirred at r.t. overnight, then concentrated and dried over oil pump to afford 1 (13.5 g, 84.1% from 1d). 1H-NMR (300 MHz, DMSO-d$_6$): δ=1.82 (d, 3H), 3.41 (s, 3H), 6.24 (q, 1H), 6.38 (d, 1H), 7.04 (s, 1H), 7.42-7.66 (m, 3H), 8.17 (s, 1H). LC-MS [M+H]$^+$: 452.0.

Example 2

Synthesis of {6-amino-5-[(2,6-dichloro-3-fluorophenyl)ethoxy]pyridazin-3-yl}-N-(1-methyl-6-oxo-1,6-dihydro-pyridin-3-yl)carboxamide

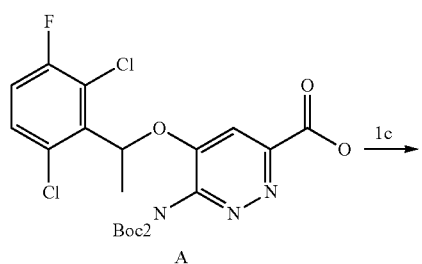

A

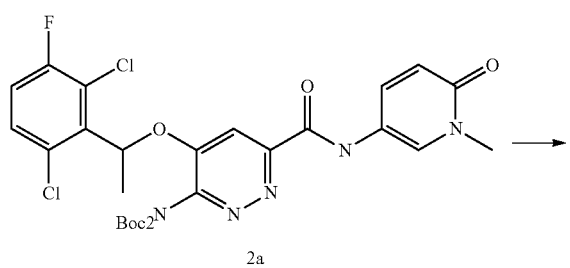

2a

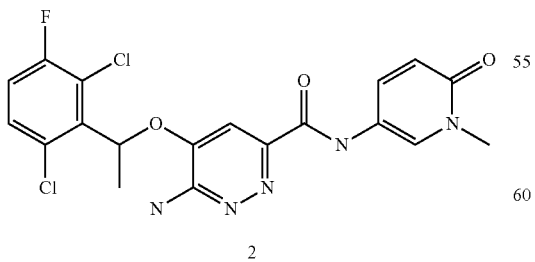

2

The procedure from A to 2 was similar to that in Example 1 (70 mg, 42% from A). 1H-NMR (300 MHz, CDCl$_3$): δ=1.89 (d, 3H), 3.57 (s, 3H), 5.40 (s, 2H), 6.21-6.27 (m, 1H), 6.59 (d, 1H), 7.06-7.12 (m, 1H), 7.26-7.37 (m, 3H), 8.28 (d, 1H), 9.40 (s, 1H). LC-MS [M+H]$^+$: 451.9.

Example 3

Synthesis of {5-[(1S)-1-(2,6-dichloro-3-fluorophenyl)ethoxy]-6-aminopyridazin-3-yl}-N-(1-methyl-6-oxo-1,6-dihydro-pyridin-3-yl)carboxamide

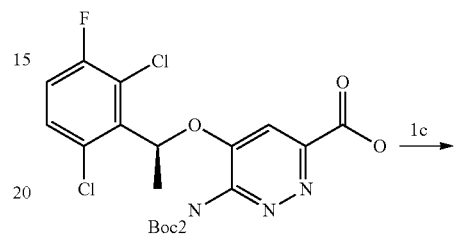

C

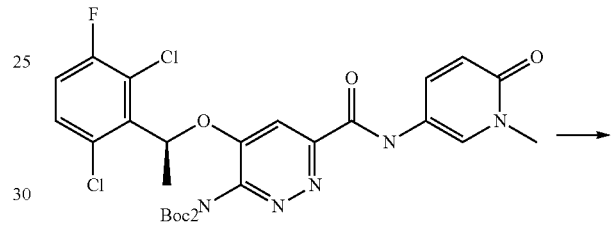

3a

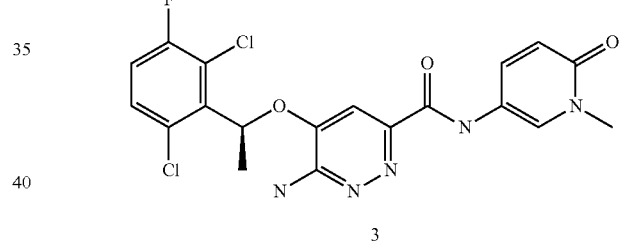

3

The procedure from C to 3 was similar to that in Example 1 to give 3 (1.29 g, yield: 71.3% from 7c). 1H-NMR (300 MHz, DMSO-d6): δ=1.86 (d, 3H), 3.42 (s, 3H), 6.27 (q, 1H), 6.41 (d, 1H), 7.06 (s, 1H), 7.52 (t, 1H), 7.61-7.70 (m, 2H), 8.23 (d, 1H), 10.47 (s, 1H). LC-MS [M+H]$^+$: 452.1.

Example 4

Synthesis of {6-amino-5-[(2,6-dichloro-3-fluorophenyl)ethoxy]pyridazin-3-yl}-N-(1-methyl-6-oxo(3-piperidyl)carboxamide

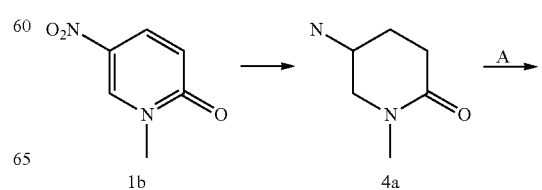

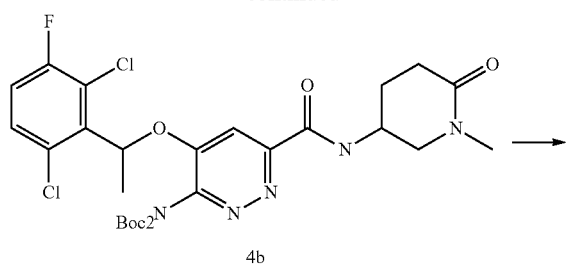

4b

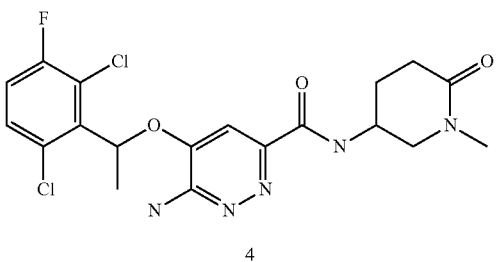

4

Step 1: To a solution of 1b in methanol was added 10% Pd/C. The mixture was hydrogenated under H2 atmosphere overnight. Pd/C was filtered off and the filtrate was evaporated to provide crude 4a which was used for next step without purification.

Step 2: The procedure from 4a to 4 was similar to that in Example 1 (131 mg, 21% from A). 1H-NMR (300 MHz, CDCl$_3$): δ=1.88 (d, 3H), 1.92-2.08 (m, 2H), 2.47-2.54 (m, 2H), 2.92 (d, 3H), 3.20-3.27 (m, 1H), 3.59-3.65 (m, 1H), 4.39-4.42 (m, 1H), 5.37 (s, 2H), 6.18-6.24 (m, 1H), 7.06-7.11 (m, 1H), 7.31-7.36 (m, 2H), 7.95 (d, 1H). LC-MS [M+H]$^+$: 457.1.

Example 5

Synthesis of {6-amino-5-[(2,6-dichloro-3-fluorophenyl)ethoxy]pyridazin-3-yl}-N-(6-oxo-1,6-dihydropyridin-3-yl)carboxamide

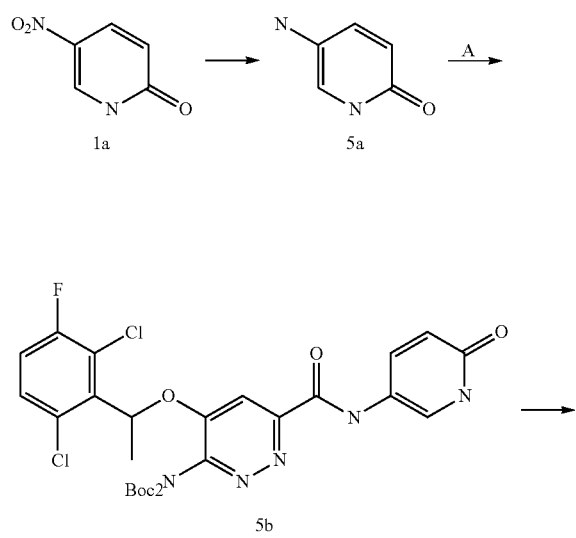

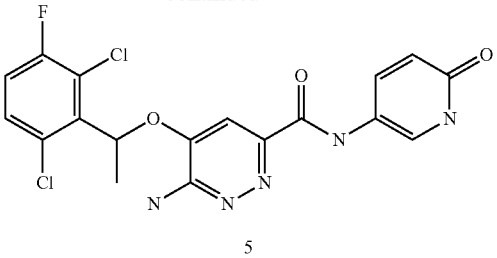

5

Step 1: The procedure from 1a to 5a was similar to that of 1b to 1c which provided 2a which was used for next step without purification.

Step 2: The procedure from 2a to 5 was similar to that in Example 1 (6.8 mg, 4.2% from 5a). 1H-NMR (300 MHz, DMSO-d$_6$): δ=1.82 (d, 3H), 6.14-6.21 (m, 1H), 6.32 (d, 1H), 6.89 (s, 2H), 6.99 (s, 1H), 7.47 (t, 1H), 7.56-7.61 (m, 1H), 7.76-7.80 (m, 1H), 7.93 (s, 1H), 10.40 (s, 1H), 11.41 (brs, 1H). LC-MS [M+H]$^+$: 437.9.

Example 6

Synthesis of {6-amino-5-[(2,6-dichloro-3-fluorophenyl)ethoxy]pyridazin-3-yl}-N-[1-(2-methoxyethyl)-6-oxo-1,6-dihydro-pyridin-3-yl]carboxamide

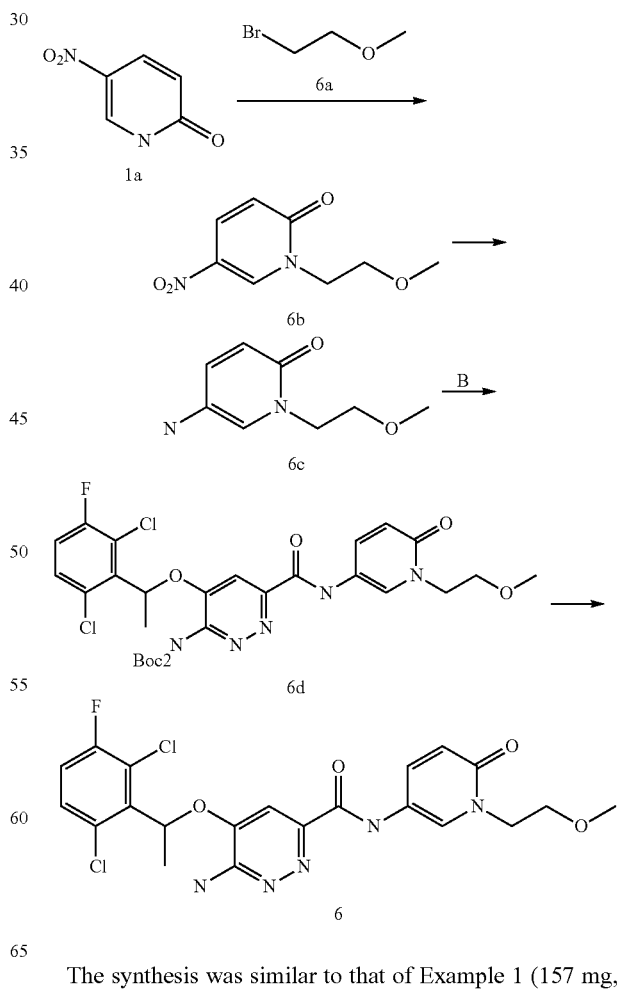

The synthesis was similar to that of Example 1 (157 mg, 56% from B). 1H-NMR (300 MHz, CDCl$_3$): δ=1.89 (d, 3H), 3.32 (s, 3H), 3.69 (t, 2H), 4.10-4.15 (m, 2H), 5.38 (s, 2H), 6.23-6.27 (m, 1H), 6.58 (d, 1H), 7.07-7.12 (m, 1H), 7.32-7.44 (m, 3H), 8.13 (d, 1H), 9.39 (s, 1H). LC-MS [M+H]⁺: 496.0.

Example 7

Synthesis of {6-amino-5-[(2,6-dichloro-3-fluorophenyl)ethoxy]pyridazin-3-yl}-N-(1-ethyl-6-oxo-1,6-dihydro-pyridin-3-yl)carboxamide

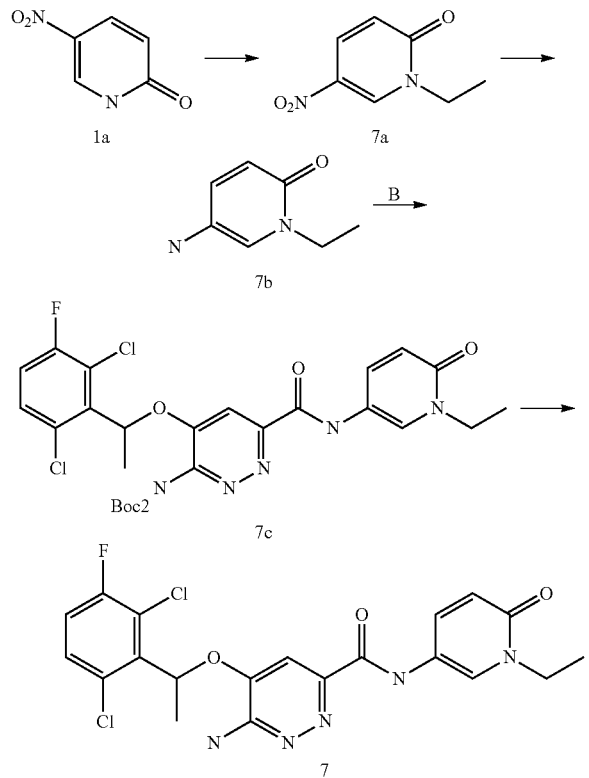

Step 1: Sodium hydride (0.63 g of a 60% dispersion in mineral oil, 15.8 mmol) is added to a solution of compound 1a (2 g, 14.4 mmol) in DMF (20 mL) at room temperature and stirred for 30 min. Ethyl iodide (2.2 g, 14.4 mmol) is added to the reaction mixture and stirred for 16 hours at room temperature. The reaction mixture is diluted with ethyl acetate, washed with water, dried over sodium sulfate and concentrated under vacuo to give compound 7a (2 g, 60%).

Step 2: A mixture of compound 7a (5 g, 29.7 mmol), Fe (6.7 g, 119 mmol) in AcOH (5 mL), water (50 mL) and MeOH (50 mL) was heated to reflux for 30 min. The solvent was removed in vacuo and the residue was purified by column chromatography to give compound 7b (2.5 g, 60%).

Step 3: To a solution of compound 7b (1 g, 7.25 mmol) in DMF (30 ml) was added HATU (4.13 g, 10.87 mmol) and compound B (20 mg, 163 mmol), DIEA (3.8 mL, 21.74 mmol), and the mixture was stirred at room temperature overnight. The reaction mixture was treated with water and extracted with EA. The organic layer was washed with brine, dried over MgSO₄ and concentrated under reduce pressure, the crude product was purified by flash chromatography (DCM:MeOH=10:1) to afford compound 7c (3.2 g, 66%).

Step 4: To the solution of compound 7c (2 g, 3 mmol) in DCM (5 mL) was added TFA (3 mL). The mixture was stirred at room temperature for 4 h and evaporated. The residue was purified by column chromatography (DCM:MeOH=20:1) to provide 7 (700 mg, 50%). 1H-NMR (300 MHz, DMSO-d6): δ=10.04 (s, 1H), 8.23-8.24 (d, 1H), 7.69-7.73 (dd, 1H), 7.56-7.61 (m, 1H), 7.44-7.50 (t, 1H), 6.97 (s, 1H), 6.92 (s, 2H), 6.33-6.37 (d, 1H), 6.15-6.18 (q, 1H), 3.85-3.92 (q, 2H), 1.80-1.82 (d, 3H), 1.17-1.22 (t, 3H), LC-MS [M+H]⁺: 467.0.

Example 8

Biological Data

Met, ALK Biochemical Assays

Kinase Assays. Assays were performed as described in Fabian et al. (2005) *Nature Biotechnology*, vol. 23, p. 329 and in Karaman et al. (2008) *Nature Biotechnology*, vol. 26, p. 127.

For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection ~0.1) and incubated with shaking at 32° C. until lysis (~90 minutes). The lysates were centrifuged (6,000×g) and filtered (0.2 mm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 mM non-biotinylated affinity ligand) and incubated at room temperature with shaking for 30 minutes. The kinase concentration in the eluates was measured by qPCR.

Most examples in this invention with $R_6$ being unsaturated heterocycle are selective c-Met inhibitors. Specifically, the R-enantiomer (e.g. Example 1) or racemic mixture (e.g. Examples 2, 5, 6, and 7) provided $IC_{50}$ values of <5 nM in this c-Met assay, while the corresponding $IC_{50}$'s for ALK were higher (>10 nM).

In contrast, the S-enantiomer (Example 3) did not show any significant inhibition at up to 50 nM in this c-Met assay.

Furthermore, the example with $R_6$ being a saturated heterocycle (Example 4) had $IC_{50}$'s of >100 nM in both of the c-Met and ALK assays, while an example (shown below) with $R_6$ being an aromatic ring was potent against both c-Met and ALK ($IC_{50}$<5 nM).

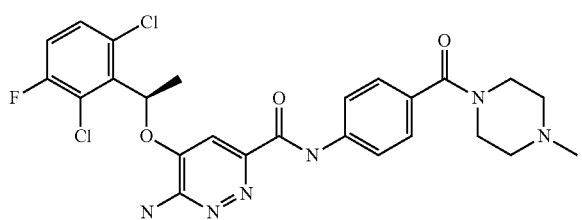 [SMILES: C[C@@H](Oc1cc(C(=O)Nc2ccc(C(=O)N3CCN(C)CC3)cc2)nnc1N)c1c(Cl)ccc(F)c1Cl]

Therefore, the R-enantiomer of compound with $R_6$ being unsaturated heterocycle (e.g. Example 1) has the surprising biological property of being a potent and selective (compared to, at least, ALK) c-Met inhibitor.

c-Met Receptor Phosphorylation Assay

A549 cells are used in this assay. Cells are seeded at a density of 40,000 cells/well in the growth media (RPMI+10% FBS) into 24-well plates and cultured overnight at 37° C. for attachment. Cells are exposed to the starvation media (RPMI+1% BSA). Dilutions of the test compounds are added to the plates and incubated at 37° C. for 1 hour. Cells are then cool down to room temperature for 15 min followed by stimulation with 40 ng/ml HGF for 15 minutes. Cells are washed once with ice-cold PBS and then lysed with 110 ul/well lysis buffer (Cell Signaling #9803+0.2% protease inhibitor, Sigma P1860) for 1 hour at 4° C. Cell lysates are transferred to microcentrifuge tubes and are spun at 10000 rpm for 10 min at 4° C. and phosphorylated HGFR is quantitated by Human Phospho-HGF R/c-Met ELISA kit (R&D, DYC2480) according to the manufacture's instructions.

In Vivo Anti-Tumor Efficacy of Compound 1 of EXAMPLE 1 Against U-87MG Tumor Xenograft Model (a) Selection of Cell Lines Based on Cellular Phosphorylation Status of c-Met HeLa, NIH-3T3, HEK293T, U87MG, PC3 and Caki were obtained from ATCC and were cultured in 10 cm plates with full growth medium. Actively proliferating cells were washed with 1×PBS once, and then lysed in the lysis buffer, pro-sonicated, and cleared by centrifugation for 10 minutes at 10,000 rpm. Total protein was measured using a BCA protein assay kit. Equal amounts of protein lysate for each cell line were loaded for western blotting.

(b) Animal:

Balb/c nude mice (6 weeks old, male) were purchased from Shanghai Slac Laboratory Animal Co. Ltd (Shanghai, China). All mice were maintained in a pathogen-free facility for ~2 weeks before implantation. They were housed in plastic cages (4~6 mice/cage) containing corn cob and maintained in a pathogen-free facility (20~25° C., 30~70% humidity) with a 12-h light:dark cycle.

(c) Xenograft Human Tumor Model:

U-87 MG xenograft model was established by implanting athymic Balb/c nude mice s.c in the right flank with U-87 MG cells, $3.6 \times 10^6$/mouse (120 ul). Tumors were allowed to reach 120~380 $mm^3$ in size.

Group and Dosage:

| Group | n | Dosage | Treatment |
|---|---|---|---|
| Vehicle Control | 8 | Formulation Vehicle | ig, BID × 11 days |
| EXAMPLE 1 | 8 | 25 mg/kg | ig, BID × 11 days |
| EXAMPLE 1 | 8 | 50 mg/kg | ig, BID × 11 days |

Note:
All treatments are given through oral gavage (10 ml/kg). For multi-dosing a day, the second dose was given 7 hours after the first one.

(d) Observation Index

Tumor volumes were measured twice a week with caliper. Tumor volumes were calculated by the formula <Tumor volume=length×width²/2>.
Percentage of tumor growth inhibition (GI) after initiation of treatment was calculated by the formula:

GI=100×{1−[(tumor volume$_{final}$−tumor volume$_{initial}$ for the compound-treated group)/(tumor volume$_{final}$−tumor volume$_{initial}$ for the vehicle-treated group)]}

Relative tumor volume is defined as the ratio of the volume at a given time and the volume at the start of treatment. The relative tumor volume (RTV) was calculated by the formula:

RTV=100×TV$_T$/TV$_0$

TV$_0$: tumor volume$_{initial}$
TV$_T$: tumor volume at T time
The relative tumor growth rate (T/C %) was calculated by the formula:

T/C %=100×T$_{RTV}$/C$_{RTV}$

T$_{RTV}$: The relative tumor volume of treatment
C$_{RTV}$: The relative tumor volume of control
Body weight of each mouse was weighed twice a week along with the tumor size measurement. The Percentage of weight loss was calculated by the formula:

Percentage of Weight Loss=100%×(Body Weight$_{initial}$−Body Weight$_{initial}$)/Body Weight$_{initial}$ The tumor weight was measured by the end of experiment. The tumor inhibitory rate (IR) was calculated by the formula:

IR=($W_C$−$W_T$)/$W_C$×100%.

(e) Results

The treatment started 24 days post tumour implantation while the average tumor volume reached 230.52±8.04 $mm^3$ (Mean±SE). After 11 days of consecutive treatment, EXAMPLE 1 at 25 and 50 mg/kg ig BID showed significant tumor growth inhibition (GI), with GI rates of 65.95% (P<0.01) and 88.71% (P<0.01) respectively. The results are summarized in Table 8.1 and FIG. 2.

TABLE 8.1

The effects of EXAMPLE 1 on the tumor volume
(mean ± S.E in $mm^3$) and GI (%)

| Days Post Implantation | d24 | d28 | d31 | d35 |
|---|---|---|---|---|
| Vehicle | 231.4 ± 25.1 | 588.7 ± 53.0 | 971.9 ± 94.8 | 1483.0 ± 158.6 |
| EXAMPLE 1, 25, BID | 230.4 ± 23.0 GI | 365.7 ± 29.3** 62.14% | 453.7 ± 19.7** 77.04% | 627.7 ± 33.9** 65.95% |

TABLE 8.1-continued

The effects of EXAMPLE 1 on the tumor volume
(mean ± S.E in mm³) and GI (%)

| Days Post Implantation | d24 | d28 | d31 | d35 |
|---|---|---|---|---|
| EXAMPLE 1, 50, BID | 230.2 ± 24.5 GI | 305.9 ± 22.0** 78.82% | 337.4 ± 27.8** 85.52% | 371.5 ± 34.4** 88.71% |

Note:
*donates P values <0.05,
**donates P values <0.01 compared with vehicle control, respectively.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed:
1. A compound of formula I:

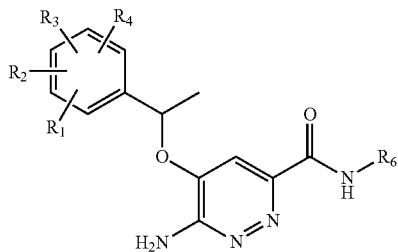

or a salt thereof; wherein:
$R_1$, $R_2$, $R_3$, and $R_4$ each are independently H, alkyl, or $Z^1$;
$R_6$ is an unsaturated heterocyclyl, wherein $R_6$ is optionally substituted by 1- 3 groups independently selected from alkyl, cycloalkyl, heterocyclyl, alkoxy, hydroxyalkyl, and $Z^1$;
Each $Z^1$ is halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)_nOH$, $(CH_2)_n$ $OR^{15}$, $(CH_2)_nC(O)NR^{15}R^{16}$, $NR^{15}S(O)_2R^{17}$, where each n is independently 0-6;
Each $R^{15}$ is independently hydrogen, $C_1$-$C_4$ alkyl or $C_3$-$C_6$ cycloalkyl;
Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl; and
Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl.

2. A compound of formula II:

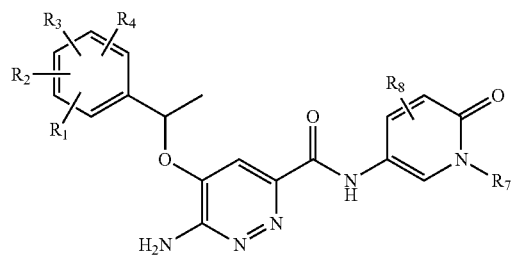

or a salt thereof; wherein
$R_1$, $R_2$, $R_3$, $R_4$, $R_7$ and $R_8$ each are independently H, alkyl or $Z^1$;
Each $Z^1$ is halogen, CN, $NO_2$, $OR^{15}$, $SR^{15}$, $S(O)_2OR^{15}$, $NR^{15}R^{16}$, $C_1$-$C_2$perfluoroalkyl, $C_1$-$C_2$perfluoroalkoxy, 1,2-methylenedioxy, $C(O)OR^{15}$, $C(O)NR^{15}R^{16}OC(O)$ $NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)_nOH$, $(CH_2)_nOR^{15}$, $(CH_2)_nC(O)NR^{15}R^{16}$, $NR^{15}S(O)_2R^{17}$, where each n is independently 0-6;
Each $R^{15}$ is independently hydrogen, $C_1$-$C_4$alkyl or $C_3$-$C_6$cycloalkyl;
Each $R^{16}$ is independently hydrogen, alkenyl, alkynyl, $C_3$-$C_6$cycloalkyl, aryl, heterocyclyl, heteroaryl, $C_1$-$C_4$alkyl or $C_1$-$C_4$alkyl substituted with $C_3$-$C_6$cycloalkyl, aryl, heterocyclyl or heteroaryl; and
Each $R^{17}$ is independently $C_3$-$C_6$cycloalkyl, aryl, heterocyclyl, heteroaryl, $C_1$-$C_4$alkyl or $C_1$-$C_4$alkyl substituted with $C_3$-$C_6$cycloalkyl, aryl, heterocyclyl or heteroaryl.

3. A compound of formula III:

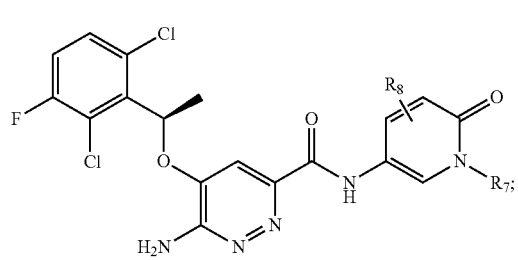

or a salt thereof; wherein
$R_7$ and $R_8$ each are independently H, alkyl or $Z^1$;
Each $Z^1$ is halogen, CN, $NO_2$, $OR^{15}$, $SR^{15}$, $S(O)_2OR^{15}$, $NR^{15}R^{16}$, $C_1$-$C_2$perfluoroalkyl, $C_1$-$C_2$perfluoroalkoxy, 1,2-methylenedioxy, $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where each n is independently 0-6;

Each $R^{15}$ is independently hydrogen, $C_1$-$C_4$ alkyl or $C_3$-$C_6$ cycloalkyl;

Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl; and Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl.

4. The compound of claim 3, wherein $R_8$ is hydrogen and $R_7$ is $C_1$-$C_3$ alkyl.

5. The compound of claim 3, wherein each $Z^1$ is independently halogen.

6. The compound of claim 1, wherein the compound is {5-[(1R)-1-(2,6-dichloro-3-fluoropheny)ethoxy]-6-aminopyridazin-3-yl}-N-(1-methyl-6-oxo-1,6-dihydro-pyridin-3-yl)carboxarnide.

7. The compound of claim 1, wherein the compound is selected from the following:

{6-amino-5[(2,6-dichloro-3-fluorophenyl)ethoxy]pyridazin-3-yl}-N-(1-methyl-6-oxo-1,6-dihydro-pyridin-3-yl)carboxamide;

{5-[(1S)-1-(2,6dichloro-3-fluoropheny)ethoxy]-6-aminopyridazin-3-yl}-N-(1-methyl-6-oxo-1,6-dihydro-pyridin-3-yl)carboxamide;

{6-amino-5-[(2,6-dichloro-3-fluorophenyl)ethoxy]pyridazin-3-yl}-N-(6-oxo-1,6-dihydro-pyridin-3-yl)carboxamide;

{6-amino-5-[(2,6-dichloro-3-fluorophenyl)ethoxy]pyridazin-3-yl}-N-[1-(2-methoxyethyl)-6oxo- 1,6-dihydro-pyridin-3-yl]carboxamide;

{6-amino-5-[(2,6-dichloro-3-fluorophenyl)ethoxy]pyridazin-3-yl}-N-(1-ethyl-6-oxo-1,6-dihydro-pyridin-3-yl)carboxamide.

* * * * *

UNITED STATES PATENT AND TRADEMARK OFFICE
CERTIFICATE OF CORRECTION

PATENT NO.        : 9,242,958 B2
APPLICATION NO.   : 13/877812
DATED             : January 26, 2016
INVENTOR(S)       : Congxin Liang It is certified that error appears in the above-identified patent and that said Letters Patent is hereby corrected as shown below:

In the Claims:

At column 36, Claim 2, line 30, please correct "$R_5$" to read -- $R_8$ --.

At column 36, Claim 2, line 34, please correct "$C(O)NR^{15}R^{16}OC(O)$" to read -- $C(O)NR^{15}R^{16}$, $OC(O)$ --.

At column 38, Claim 6, line 4, please correct the word "carboxarnide" to read -- carboxamide --.

At column 38, Claim 6, line 10, please correct the word "2,6dichloro" to read -- 2,6-dichloro --.

At column 38, Claim 6, line 16, please correct the word "6oxo" to read -- 6-oxo --.

Signed and Sealed this
Twenty-sixth Day of April, 2016

Michelle K. Lee
*Director of the United States Patent and Trademark Office*